US009969780B1

(12) United States Patent
Ensoli

(10) Patent No.: US 9,969,780 B1
(45) Date of Patent: May 15, 2018

(54) TAT COMPLEXES, AND VACCINES COMPRISING THEM

(75) Inventor: Barbara Ensoli, Rome (IT)

(73) Assignee: Istituto Superiore di Sanita, Rome (IT)

( * ) Notice: Subject to any disclaimer, the term of this patent is extended or adjusted under 35 U.S.C. 154(b) by 626 days.

(21) Appl. No.: 10/597,926

(22) PCT Filed: Mar. 11, 2005

(86) PCT No.: PCT/EP2005/003043
§ 371 (c)(1),
(2), (4) Date: May 3, 2007

(87) PCT Pub. No.: WO2005/090391
PCT Pub. Date: Sep. 29, 2005

(30) Foreign Application Priority Data

Mar. 11, 2004 (GB) .................................. 0405480.5

(51) Int. Cl.
| C07K 14/16 | (2006.01) |
| A61K 39/21 | (2006.01) |
| A61K 38/17 | (2006.01) |
| C07K 14/73 | (2006.01) |

(52) U.S. Cl.
CPC .......... C07K 14/16 (2013.01); A61K 38/1774 (2013.01); A61K 39/21 (2013.01); C07K 14/162 (2013.01); C07K 14/163 (2013.01); C07K 14/70514 (2013.01); G01N 2469/20 (2013.01)

(58) Field of Classification Search
None
See application file for complete search history.

(56) References Cited

U.S. PATENT DOCUMENTS

2003/0157135 A1* 8/2003 Tsuji et al. .................. 424/278.1

FOREIGN PATENT DOCUMENTS

| EP | 0567643 | 11/1993 |
| EP | 1431306 | 6/2004 |
| JP | 2001286284 | 10/2001 |
| JP | 2003277262 | 10/2003 |
| WO | WO 01/54719 | 8/2001 |
| WO | WO 02/080917 | 10/2002 |
| WO | WO 02/087614 | * 11/2002 |
| WO | 03/009867 A1 | 2/2003 |
| WO | 2004/041851 A2 | 5/2004 |
| WO | WO 2005/039631 | 5/2005 |

OTHER PUBLICATIONS

Voss et al., Prevention of Disease Induced by a Partially Heterologous AIDS Virus in Rhesus Monkeys by Using an Adjuvanted Multicomponent Protein Vaccine, 2003, 77(2);1049-1058.*
Sattentau et al., Conformational Changes Induced in the Envelope Glycoproteins of the Human and Simian Immunodeficiency Viruses by Soluble Receptor Binding, Journal of Virology, 1993, 67(12):7383-7393.*
Ibrahim et al., Cell-surface heparan sulfate facilitates human immunodeficiency virus Type 1 entry into some cell lines but not primary lymphocytes, Virus Research, 1999, 60:159-169.*
Watanabe et al., Efficacy of chemically cross-linked antigens for acellular pertussis vaccine, Vaccine, 2000, 19(9-10):1199-1203.*
Caselli et al., J. Immunol., 1999, 162:5631-5638.*
Chang et al., Vaccine, 1999, 17:1540-1548.*
Borbe et al., Journal of Peptide Science, 1995, 1:109-123.*
GenBank Accession No. P69697 (Aug. 13, 1987).*
Fouts et al., PNAS, 2002, 99(18):11842-11847.*
Kang et al., Journal of Virology, 1994, 68(9):5854-5862.*
Gzyl et al. (Jan. 2004) "Effect of Partial and Complete Variable Loop Deletions of the Human Immunodeficiency Virus Type 1 Envelope Glycoprotein on the Breadth of gp160-Specific Immune Responses," Virology 318(2):493-506.
Lee et al. (Apr. 2, 1999) "Epitope Mapping of CCR5 Reveals Multiple Conformational States and Distinct bu Overlapping Structures Involved in Chemokine and Coreceptor Function," J. Biol. Chem. 274(14):9617-9626.
O'Brien et al. (May 1996) "Anti-Human Immunodeficiency Virus Type 1 Activity of an Oligocationic Compound Mediated via gp120 V3 Interactions," J. Virol. 70(5):2825-2831.
Penman et al. (1993) "Omeprazole Inhibits Colorectal Carcinogenesis Induced by Azoxymethane in Rats," Gut 34:1559-1565.
Sartippour et al. (2003) "The Effect of Commonly Used Drugs on Angiogenesis," Anticancer Res. 23:231-234.
Wyatt et al. (1995) "Involvement of the V1/V2 Variable Loop Structure in the Exposure of Human Immunodeficiency Virus Type 1 gp120 Epitopes Induced by Receptor Binding," J. Virol. 69:5723-5733.
Translation of "Notice of Reasons of Rejection", Jan. 20, 2010, 5 pp., for JP 2007/502311.
Rusnati, Marco, "Interaction of HIV-1 Tat Protein with Heparin", J. Biol. Chem, Apr. 1997, p. 11313-11320, vol. 272, No. 17, The American Society for Biochemistry and Molecular Biology, Inc.
Mitola, Stefania, "Identification of Specific Molecular Structures of Human Immunodeficiency Virus Type 1 Tat Relevant for Its Biological Effects on Vascular Endothelial Cells", J. Virol., Jan. 2000, p. 344-353, vol. 74, No. 1, American Society for Microbiology.
Examination Report (Communication pursuant to Article 94(3) EPC) in corresponding European Application No. EP 05 729 692.0, Completed Oct. 16, 2009.
Moulard et al. (May 14, 2002) "Broadly Cross-Reactive HIV-1-Neutralizing Human Monoclonal Fab Selected for Binding to gp120-CD4-CCR5 Complexes," Proc. Nat. Acad. Sci. USA 99(10):6913-6918.
Barnett, S. W. et al. (2001)"The Ability of an Oligomeric Human Immunodeficiency Virus Type 1 (HIV-1) Envelope Antigen to Elicit Neutralizing Antibodies against Primary HIV-1 Isolates Is Improved following Partial Deletion of the Second Hypervariable Region," J. Virology, 75(12):5526-5540.
Center, R. J. et al. (2002) "Oligomeric Structure of the Human Immunodeficiency Virus Type 1 Envelope Protein on the Virion Surface," J. Virology, 76(15):7863-7867.

(Continued)

Primary Examiner — Nicole Kinsey White
(74) Attorney, Agent, or Firm — HoustonHogle LLP

(57) ABSTRACT

Complexes comprising HIV Tat and the V3 loop from gp120 Env provide novel epitopes and are immunogenic to prevent or inhibit infection by HIV.

23 Claims, No Drawings

(56) References Cited

OTHER PUBLICATIONS

Earl, P.L. et al. (1994) "Native Oligomeric Human Immunodeficiency Virus Type 1 Envelope Glycoprotein Elicits Diverse Monoclonal Antibody Reactivities," J. Virology, 68(5):3015-3026.

Earl, P.L. et al. (2001) "Immunogenicity and Protective Efficacy of Oligomeric Human Immunodeficiency Virus Type 1 gp140," J. Virology, 75(2):645-653.

Fouts, T.R. et al. (1997) "Neutralization of the Human Immunodeficiency Virus Type 1 Primary Isolate JR-FL by Human Monoclonal Antibodies Correlates with Antibody Binding to the Oligomeric Form of the Envelope Glycoprotein Complex," J. Virology, 71(4):2779-2785.

Gorny, M. K. et al. (2000) "Effects of Oligomerization on the Epitopes of the Human Immunodeficiency Virus Type 1 Envelope Glycoproteins," Virology 267:220-228.

Liu, L. et al. (Dec. 2011) "Intraprotomer masking of third variable loop (V3) epitopes by the first and second variable loops (V1V2) within the native HIV-1 envelope glycoprotein trimer," Proc. Nat'l Acad. Sci (USA) 108(50):20148-20153.

Monini, P. et al. (Nov. 2012) "HIV-1 Tat Promotes Integrin-Mediated HIV Transmission to Dendritic Cells by Binding Env Spikes and Competes Neutralization by Anti-HIV Antibodies," PLOS One 7(11):e48781.

Pancerra M. & Wyatt, R. (Dec. 2004) "Selective recognition of oligomeric HIV-1 primary isolate envelope glycoproteins by potently neutralizing ligands requires efficient precursor cleavage," Virology 332:145-156.

Rusert, P. et al. (Jun. 2011) "Interaction of the gp120 V1V2 loop with a neighboring gp120 unit shields the HIV envelope trimer against cross-neutralizing antibodies," J. Experimental Medicine, 208(7):1419-1433.

Srivastava, I. K. et al. (Oct. 2003) "Purification, Characterization, and Immunogenicity of a Soluble Trimeric Envelope Protein Containing a Partial Deletion of the V2 Loop Derived from SF162, an R5-Tropic Human Immunodeficiency Virus Type 1 Isolate," J. Virology, 77(20) 11244-11259.

Stamatatos L. & Cheng-Mayer, C. (1995) Structural Modulations of the Envelope gp120 Glycoprotein of Human Immunodeficiency Virus Type 1 upon Oligomerization and Differential V3 Loop Epitope Exposure of Isolates Displaying Distinct Tropism upon Virion-Soluble Receptor Binding, J. Virology, 69(10):6191-6198.

Yang, X. et al. (2000) "Modifications That Stabilize Human Immunodeficiency Virus Envelope Glycoprotein Trimers in Solution," J. Virology, 74(10):4746-4754.

Yang, X. et al. (2001) "Improved Elicitation of Neutralizing Antibodies against Primary Human Immunodeficiency Viruses by Soluble Stabilized Envelope Glycoprotein Trimers," J. Virology, 75(3):1165-1171.

Yang, X. et al. (May 2002) "Highly Stable Trimers Formed by Human Immunodeficiency Virus Type 1 Envelope Glycoproteins Fused with the Trimeric Motif of T4 Bacteriophage Fibritin," J. Virology, 76(9):4634-4642.

Binley et al. (Dec. 2004) "Comprehensive cross-clade neutralization analysis of a panel of anti-human immunodeficiency virus type 1 monoclonal antibodies," J. Virol. 78(23):13232-13252.

Fanales-Belasio (2002) "Native HIV-1 Tat protein targets monocyte-derived dendritic cells and enhances their maturation, function, and antigen-specific T cell responses," J. Immunol. 168:197-206.

Kiszka et al. (2002) "Effect of the V3 loop deletion of envelope glycoprotein on cellular responses and protection against challenge with recombinant vaccinia virus expressing gp160 of primary human immunodeficiency virus type 1 isolates," J Virol. 76(9):4222-4232.

Lu et al. (1998) "Rhesus macaques that become systemically infected with pathogenic SHIV 89.6-PD after intravenous, rectal, or vaginal inoculation and fail to make an antiviral antibody response rapidly develop AIDS," Journal of Acquired Immune Deficiency Syndromes and Human Retroviruses. 19:6-18.

Monini et al. (Nov. 13, 2012) "HIV-1 tat promotes integrin-mediated HIV transmission to dendritic cells by binding Env spikes and competes neutralization by anti-HIV antibodies," PLoS One. 7(11):e48781. Supplementary Figure 8.

Pierleoni et al. (Aug. 20, 2010) "Effect of the redox state on HIV-1 tat protein multimerization and cell internalization and trafficking," Mol. Cell. Biochem.

Stamatatos et al. (1998) "An envelope modification that renders a primary, neutralization-resistant clade B human immunodeficiency virus type 1 isolate highly susceptible to neutralization by sera from other clades," J. Virol. 72(10):7840-7845.

Vyas et al. (Aug. 2008) "The known unknowns of antigen processing and presentation," Nature Reviews. 8:607-618.

Cardaci et al. (Sep. 17, 2013) "The V1/V2 Loop of HIV-1 gp120 is necessary for Tat binding and consequent modulation of virus entry," FEBS Letters. 587(18):2943-2951.

Cimbro et al. (Feb. 25, 2014) "Tyrosine sulfation in the second variable loop (V2) of HIV-1 gp120 stabilizes V2—V3 interaction and modulates neutralization sensitivity," Proc. Natl. Acad. Sci. USA. 111(8):3152-3157.

Fouts et al. (1998) "Interactions of Polyclonal and Monoclonal Anti-Glycoprotein 120 Antibodies with Oligomeric Glycoprotein 120-Glycoprotein 41 Complexes of a Primary HIV Type 1 Isolate: Relationship to Neutralization," Aids Research and Human Retroviruses. 14(7):591-597.

Huang et al. (2005) "Structure of a V3-containing HIV-1 gp120 core," Science. 310(5750)1025-1028.

Huang et al. (2007) "Structures of the CCR5 N terminus and of a tyrosine-sulfated antibody with HIV-1 gp120 and CD4," Science. 317(5846):1930-1934.

Kwon et al. (Apr. 10, 2012) "Unliganded HIV-1 gp120 core structures assume the CD4-bound conformation with regulation by quaternary interactions and variable loops," Proc. Natl. Acad. Sci. USA. 109(15):5663-5668.

Lu et al. (1998) "Short Communication: Immunogenicity of DNA Vaccines Expressing Human Immunodeficiency Virus Type 1 Envelope Glycoprotein with and without Deletions in the V1/2 and V3 Regions," Aids Research and Human Retroviruses. 14(2):151-155.

Mollica et al. (Sep. 9, 2016) "Binding Mechanisms of Intrinsically Disordered Proteins: Theory, Simulation, and Experiment," Frontiers in Molecular Biosciences. 3:52. pp. 1-18.

Poon et al. (Sep. 24, 2013) "Putative role of Tat-Env interaction in HIV infection," AIDS. 27(15):2345-2354.

To et al. (Feb. 11, 2016) "The Dynamic Landscape of the Full-Length HIV-1 Transactivator of Transcription," Biochem. 55:1314-1325.

Agwale, S. M. et al., "A Tat Subunit Vaccine Confers Protective Immunity Against the Immune-Modulating Activity of the Human Immunodeficiency Virus Type-1 Tat Protein in Mice," Proceedings of the National Academy of Science of USA, vol. 99, No. 15, Jul. 23, 2002, pp. 10037-10041. Five pages.

International Search Report and the Written Opinion of the International Searching Authority, dated Aug. 4, 2005, from International Application No. PCT/EP2005/003043, filed on Mar. 11, 2005. Fifteen pages.

International Preliminary Report on Patentability, completed on Jun. 22, 2006, from International Application No. PCT/EP2005/003043, filed on Mar. 11, 2005. Seventeen pages.

* cited by examiner

TAT COMPLEXES, AND VACCINES COMPRISING THEM

CROSS REFERENCE TO RELATED APPLICATIONS

This application is a National Stage (371) of International Application No. PCT/EP2005/003043, filed Mar. 11, 2005, which claims priority to United Kingdom Patent Application 0405480.5, filed Mar. 11, 2004.

The present invention relates to the use of protein materials comprising the gp120 V3 loop in the manufacture of a vaccine against viruses expressing gp120.

HIV adsorption to the membrane of target cells occurs upon the interaction of HIV gp120 with the cell receptor, CD4. This interaction induces a conformational transition in gp120, leading to the exposure of the gp120 V3 loop. According to one proposed model, the gp120 V3 loop interacts, in turn, with other cell surface molecules acting as co-receptors for HIV. The most important HIV co-receptors are the chemokine receptors CCR5 and CXCR4. It is now generally accepted that macrophage-tropic (M-tropic) HIV isolates infect macrophages via CCR5, while T cell line tropic (TCL-tropic) HIV strains infect TCL via CXCR4, and dual-tropic strains infect via either of the co-receptors.

The interaction of the gp120 V3 loop with the co-receptors for HIV allows the formation of a ternary complex between the co-receptor, CD4 and gp120 leading, in turn, to conformational changes in gp41. Together with gp120, gp41 forms the virus envelope glycoprotein complex (Env). These conformational changes are believed to be required in order to expose the fusing sequence at the N terminus of gp41, which interacts with the cell surface and leads to fusion between the virus envelope and the cell membrane. In the course of this stepwise mechanism, cryptic epitopes on gp41 and gp120 are exposed as a result of the interaction between gp120 and CD4. These epitopes are otherwise hidden, and, in case of gp120, are recognised by antibodies directed against the portion of gp120 interacting with the co-receptors.

These cryptic epitopes have been the object of intense research for vaccination and passive-immunisation purposes, and there is considerable evidence that the gp120 V3 loop is involved in co-receptor recognition and usage. In particular: point mutations or deletions in V3 have been shown to abrogate or shift co-receptor usage; V3 peptides have been proven to interact with CXCR4; and antibodies against V3 can impair or block gp120-CCR5 binding. This model is, therefore, generally accepted, although various observations have lead to the notion that additional events are involved in co-receptor utilisation, particularly in macrophages.

Tat is a regulatory protein associated with human immunodeficiency virus type 1 (HIV-1), produced very early after infection, and which is essential for virus gene expression, replication and infectivity (Arya 1985; Fisher 1986; Chang 1995). During acute infection of T cells by HIV, Tat is also released in the extracellular milieu and taken up by neighbour cells (Frankel 1988; Ensoli 1990; Ensoli 1993; Chang 1997) where, depending on the concentration, conformational state, and cell type, it can increase virus infectivity. Specifically, uptake of Tat can enhance, in infected cells, virus gene expression and replication (Frankel 1988; Ensoli 1993; Chang 1997), while, in uninfected cells, it enhances the expression of both co-receptors CCR5 and CXCR4, favouring transmission of both macrophage and T lymphocyte-tropic HIV-1 strains (Huang 1998; Secchiero 1999).

Consistent with these findings, the immune response to Tat has been shown to play a key role in controlling the progression of AIDS and AIDS-associated diseases, and to protect Tat-vaccinated monkeys from SHIV infection (Cafaro et al., Nat Med 1999). However, no specific role of Tat in the molecular events mediating HIV adsorption or membrane fusion has been ever recognised or postulated, on the basis of the available studies.

WO 01/54719 discloses the use of Tat and/or Nef, as antigens, in the form of functional, inactivated, mutated, or as antigenic peptides, together with wild type Env, based on the observation that the combination of these antigens is useful in protecting vaccinated monkeys against challenge with SHIV. Derivatisation of the antigens to the antigenic forms described makes them safer and/or more stable. There is no suggestion that a complex between Tat, or Nef, and Env is formed.

Surprisingly, we have found that Tat can interact with the gp120 V3 loop, thereby mimicking the CCR5 co-receptor, both at the molecular (structural) and functional level, thereby conferring on CCR5-tropic HIV strains the ability to infect cell targets expressing only very low amounts of CCR5, and which would not be infected with the same virus input, in the absence of immobilised Tat.

Thus, in a first aspect, there is provided a complex comprising first and second peptides, the first peptide comprising the V3 loop of gp120, the V3 loop being available to coordinate with a binding region on the second peptide, the binding region being derived from Tat and being recognisable by the monoclonal antibody directed against the CCR5 second extracellular loop described by Lee, B., et al., J. Biol. Chem., 1999, Vol. 274, 9617-9626, for use in therapy. The monoclonal antibody identified is available from Pharmingen under catalogue no. 36460D.

In an alternative aspect, the present invention provides a complex comprising first and second peptides, the first peptide comprising the V3 loop of gp120, the V3 loop being available to coordinate with a binding region on the second peptide, the binding region comprising at least residues 21-40 and 46-60, or 21-60, of SEQ ID NO 1, or a fragment, mutant or variant thereof, capable of binding residues 301-419 of SEQ ID NO. 2.

Preferably, the binding region consists of at least residues 21-58 of SEQ ID NO 1. Preferably, residues 21-48 and 46-60, or 46-58, of SEQ ID NO 1 are linked by a suitable linker and are suitably positioned so that they are capable of binding residues 301-419 of SEQ ID NO. 2. Alternatively, a single contiguous stretch comprising 21-58 of SEQ ID NO 1 is also preferred, again provided that the ability to bind residues 301-419 of SEQ ID NO. 2 is retained Preferably, the binding region comprises at least residues 21-58 of SEQ ID NO 1. Alternatively, it is also preferred that the binding region comprising at least residues 21-40 and 46-58 of SEQ ID NO 1.

The invention further provides a complex comprising first and second peptides, the first peptide comprising the V3 loop of gp120, the V3 loop being available to coordinate with a binding region on the second peptide, the binding region being derived from Tat and being recognisable by an anti-CCR5 antibody, for use in therapy, particularly for use as an immunogenic component in a vaccine.

It will be understood that the term 'peptide' is used herein to denote a substance having peptide or peptidomimetic linkages therein, and which may be part of a larger molecule comprising other types of compound, such as sugar residues. It is generally preferred that the peptide comprise a majority of the naturally occurring amino acids, and it is particularly preferred that naturally occurring amino acids form in excess of 90% of the peptides. In one preferred embodiment, the peptides consist of naturally occurring peptides, optionally substituted by blocking groups at either or both termini and/or glycosidic residues.

It is particularly surprising that Tat is able to bind the V3 loop of gp120 and that, furthermore, the region of Tat that binds the V3 loop is recognisable by anti-CCR5 antibodies. Given the exceedingly high specificity of monoclonal antibodies, it is highly likely that the effect of Tat on the V3 loop of gp120 is similar, or identical, to that of CCR5. Indeed, we have established that extracellular Tat is effectively able to provide CCR5 functionality to T cells that express very low amounts of this co-receptor, at least insofar as HIV infectivity is concerned.

With regard to WO 01/54719, for example, although Tat and Env may be administered together, Tat is not able to bind the V3 loop of Env in the preparation, as Env has not been activated by CD4, and as specific precaution are not taken in order to avoid perturbation of the Tat V3 loop interaction, such as complex cross linking or addition of the adjuvant only after the complex is formed. In case of WO 01/54719, by the time that Env is activated by CD4, it will no longer be in proximity to Tat, so that the only advantage to be gained from joint administration is the known advantage of Tat as an adjuvant. In the present invention, not only can Tat, especially where present, as such, act as an adjuvant, but its association with the V3 loop creates a novel antigenic epitope or epitopes useful in protecting against HIV infection, or the against the spread of infection.

Thus, M-tropic HIV strains will initially target only macrophages but, once Tat is released, even T cells expressing very small amounts of CCR5 can rapidly be infected, which can lead to the massive build up of virus necessary to establish persistent infection.

By recognising this, it is now possible to provide an antigenic complex of at least the relevant parts of Tat and Env, thereby to stimulate an immunogenic response in an individual, for prophylaxis or therapy.

Such complexes may also be used to generate antibodies for use in passive immunisation, such as where it is suspected that an individual may have been exposed to HIV. Such antibodies may be raised in animals for use in humans, and may also be sequenced and humanised by methods well known in the art.

While complexes, and antibodies against them, are of particular use against CCR5-tropic viral strains, they may also be employed against TCL-tropic strains to hamper, or even block, Tat-mediated spread of the virus from one T cell to another. Likewise, dual-tropic strains may also be targeted.

Owing to the molecular mimicry of CCR5 by Tat, complexes and antibodies generated against these complexes will also, in part, mimic or be directed against epitopes present in CCR5 or in the CCR5/V3 loop complex, contributing further to the efficacy of the vaccine or antibodies used in passive immunisation.

A complex of the present invention may generally be suitably provided as a combination of two peptide species in a vehicle suitable for injection. The vehicle containing the complex may be stored as such, or may be provided as separate preparations of the individual peptides and/or vehicle for combination prior to use.

The complex of the present invention will typically comprise the two peptide species in contact with each other. Whilst it is preferred, it is not necessary that the two species be present in stoichiometric amounts, nor that even a majority of either species be complexed or bound to the other. All that is required is that a sufficient amount of an antigenic combination of the two species be presented in order to be able to stimulate an immune response thereagainst.

The complex of the present invention may rely simply on the natural interaction between Tat and the V3 loop of gp120. Weaker complexes may also be employed, but it is generally preferred to strengthen the complex. In this respect, for example, it is possible to employ the disulphide bridges that can occur in association with the cysteine-reach region of the Tat protein, or to use other protein cross-linking technologies that are known in the art such as, for example, the BS3 cross-linker.

The complex may simply comprise the relevant areas of Tat and gp120. In the case of gp120, all of, or a substantial part of, the V3 loop region, is sufficient although, as indicated by molecular docking data, residues proximal to the V3 loop may also be involved, in vivo. In the case of Tat, while amino acids 1 to 61 and, possibly, up to amino acid 70 and beyond, are involved in binding with the V3 loop, it appears particularly advantageous to employ residues 21 to 58. This stretch of the Tat sequence binds particularly strongly to the monoclonal anti-CCR5 antibody.

That part of the Tat molecule that appears generally to be important, in the present invention, comprises residues 1, 2, 4, 16, 19-22, 25, 26, 29, 34, 35, 45-47, 51, 55, 57, 59, and 61, with reference to SEQ ID NO 1. However, anti-CCR5 strongly recognises the Tat (21-58) peptide and, less strongly, the Tat (46-60) peptide, which encompasses the basic region of Tat. The fragment of Tat from residue 21 to 58 is known to contain two important functional domains of the protein: the cystein rich region (21-40) and the basic region (46-58). The Tat (21-58) peptide, but not 21-40, i.e. cystein rich region, is also the minimal peptide required for Tat-mediated expansion of HIV tropism to low CCR5 expressing TCLs. These data strongly predict that the Tat cystein rich region is required for best conformational structure of the basic region of Tat for CCR5 mimicry. Thus, where less than full length Tat is employed in the present invention, then it is preferred to employ at least residues 21-58 or 21-60, with truncated peptides of intermediate length, or at least residues 21-40 and 46-58 to be both present, jointed together or through a linker region, in a single recombinant peptide, and preferably also forming a part of the invention. Where a mutant or variant of the above sequence is used, then this may vary by deletion, insertion or inversion of one or more residues, provided that the resulting peptide is capable of binding the V3 loop of naturally occurring gp120 as determined in accordance with the assay described in the accompanying Examples. Preferred residues to retain are, as appropriate: 1, 2, 4, 16, 19-22, 25, 26, 29, 34, 35, 45-47, 51, 55, 57, 59, and 61.

SEQ ID NO 1 shows the entire amino acid sequence of Tat.

It will be appreciated that carrier peptides or framework molecules may comprise the relevant part of Tat, but this may create other epitopes, so is not generally preferred, where the creation of extra epitopes is not intended.

The peptide comprising the V3 loop may comprise or consist of gp120, optionally truncated and/or with deletions, or may comprise a larger or smaller molecule. In one preferred embodiment, the peptide comprising the V3 loop may comprise some or all of Env. In this regard, Env in its native form, is taken as being the unprocessed protein produced by the virus as a fusion protein between gp120-gp41, and is also known as gp160. The peptide may also comprise fragments of Env, and it will be understood that Env, as used herein, refers not just to Env and its fragments, but to any peptide expressing, or capable of expressing, the V3 loop. For reference, the complete sequence of gp120 is provided herein as SEQ ID NO 2. In this context, it will be appreciated that the peptide may consist simply of the V3 loop region, and may also consist of any intermediate molecule, such as a carrier molecule expressing or exposing one or more V3 loops, as discussed elsewhere herein.

The Env molecule or complex may be that which occurs in nature, or may be any deletion or variation thereon, provided that it still contains the V3 loop. Deletion mutants are preferred, such as the ΔV2Env mutant, which lacks the V2 loop but which retains part of gp41. This mutant has been found to provide particularly good results in combination with Tat, yielding high anti-Env antibody titres. In an embodiment, a complex of the invention has all or part of gp160 as a component thereof, the gp160 comprising at least the V3 loop of gp120 and lacking at least the majority of the V2 loop of gp120.

ΔV2Env forms a complex with Tat, and increases the humoral response against Env, without suppressing that against Tat. By way of contrast, wild type Env forms a complex, but does not increase the humoral response against Env, and suppresses those against Tat, thereby demonstrating that use of ΔV2Env stimulates a greater B cell repertoire than wild type Env.

Thus, in a preferred embodiment, a complex of the invention has ΔV2Env as a component thereof.

The V3 loop containing region of Env preferably comprises at least residues 3 01-412 of SEQ ID NO. 2, and may comprise any variation or mutation on that sequence, such as by deletion, insertion or inversion of one or more amino acids, provided that the resulting loop is capable of binding Tat as shown in SEQ ID NO. 1, as determined by the assay in the accompanying Examples. More preferably, any V3 loop-containing sequence comprises at least residues 301, 316, 317, 318, 321, 322, 324, 325, 327, 328, 329, 331, 332, 405, 407, 412, 416-419 as shown in SEQ ID NO. 2. However, the V3 loop itself, comprising nucleotides 299-333 in SEQ ID NO. 2, is also object of the invention.

It is known that Tat can function as an adjuvant, increasing cell-mediated immune responses against antigens, and polarising the immune response toward a Th1 phenotype (Fanales Belasio et al., J Immunol 2002; Ensoli B., WO03/009867). In addition, Tat broadens Th1 responses against antigens by altering their processing by the proteasome (Ensoli et al., PCT/EP2004/11950). This results in the induction of responses against antigenic cytotoxic T cell (CTL) epitopes that are normally sub-dominant (Ensoli et al., PCT/EP2004/11950).

What we have found is that these properties are not affected, so that the use of Tat with Env stimulates a broader response against sub-dominant epitopes, even of Env, but also that other antigens can be administered therewith.

More preferably, any molecule or substance capable of interacting with Env to expose a functional V3 loop may usefully be employed in the present invention, in order to stimulate antibody production, for example. In this case, a functional V3 loop is capable of binding Tat as shown in SEQ ID NO. 1, as determined by the assay in the accompanying Examples.

A suitable example is CD4 or a fragment thereof capable of causing exposure of the V3 loop on interaction with Env. Also included are envelope components, and fragments thereof, of the virus particles that, upon binding of Tat to the virus surface, will react by inducing the exposure of the V3 loop present in Env.

It is known that the V3 loop is the major determinant for the binding of Env to the heparan sulphates that are present in the extracellular matrix and cell membranes. It is also known that Tat binds through its basic region to heparan sulphates. Accordingly, now that it has been demonstrated that Tat and Env form a complex, the present invention further extends to complexes further comprising a heparan sulphate, optionally together with other molecules known to bind heparan sulphates, and which are associated with infection/inflammation sites. Such further molecules may include basic fibroblast growth factor, for example, and the complexes are especially for use as an immunogen for vaccination.

Since it is known in the field that Tat binds integrins, which are cellular adhesion receptors, including $\alpha_v\beta_3$, $\alpha_v\beta_5$, and which mediate Tat entry into cells, the present invention further extends to a complex of the invention, with an integrin as a further component, especially for use as an immunogen for vaccination. Other molecules useful in forming complexes for use in the present invention include molecules and substances that bind either Tat or Env, or both, and may include CD26, VEGF receptors, and chemokine receptors, for example.

What is important is that the complex be adequate to stimulate an immune response such that antibodies raised thereby will recognise the Tat/Env complex in vivo. Thus, while it is generally possible to employ variants of the Tat sequence to bind the gp120 V3 loop, it is possible that antibodies raised against the resulting complex will not recognise the complex of Tat or $Tat_{21-58}$ and Env in vivo, where the tertiary configuration of the complex of the Tat peptide and loop differs from that of the complex formed between Tat or $Tat_{21-58}$ and Env, in vivo.

Thus, it is generally preferred that the complex employed for raising antibodies, or as an immunogen in a vaccine preparation, comprises substantially the full sequence of Tat, or preferably at least $Tat_{21-58}$, in an immunologically natural conformation. In this regard, it is possible to make certain amino acid substitutions without affecting the immunogenicity of Tat, although such substitutions may affect the biological efficacy of the resulting Tat in other ways. It may be desirable to make such substitutions for reasons such as ensuring greater binding between Tat and the V3 loop, for example, or such substitutions may result from preferred genetic engineering processes.

For complex formation, it is less important that the V3 loop be part of the overall Env molecule, and this loop may be provided in a suitable context in a carrier molecule, provided that it is available in such a fashion as to be able to form a complex with the Tat peptide. In particular, it will be appreciated that such a carrier molecule may express more than one V3 loop to form a multimeric complex with various Tat proteins.

In general, it is preferred that naturally occurring Env, or a similar or related protein, such as a variant or engineered mutant thereof, be employed, provided that, conformationally, it exposes the V3 loop. This exposure may be achieved by adding CD4, or the gp120 binding epitope of CD4, for example, and may optionally include heparan sulphates, to a preparation of the other two peptide species, preferably in such a manner that the components can be linked as a fusion protein, or by chemical cross-linking, for example, thus enabling gp120 to expose the V3 loop in such a system.

In a preferred aspect, the present invention provides use of a complex as described above in the preparation of a medicament for the treatment or prophylaxis of a viral infection, whereby the infecting virus expresses a molecule capable of forming a ternary complex between itself, CD4 and CCR5.

The peptides used in the complex may be derivatised or substituted in any conventional manner, provided that they are still able to perform their desired purpose, as described above. In particular, especially where the peptides are short, the N- and/or C-terminals may be chemically blocked to inhibit the action of peptidases, for example. Where the peptides are chemically synthesised or semi-synthesised, it may also be desirable to substitute susceptible bonds with a moiety less susceptible to attack. In some cases, it may be appropriate to substitute large tracts of the peptides with peptidomimetic groups.

In a preferred complex of the invention, the second peptide comprises the HIV Tat cysteine and basic region and the first peptide comprises the V3 loop of HIV Env. The second peptide may comprise HIV Tat fragments or derivatives thereof and the first peptide may comprise HIV Env fragments or derivatives thereof. The second peptide may comprise HIV Tat peptides or epitopes, and the first peptide may comprise HIV Env peptides or epitopes.

In a preferred embodiment, complexes of the invention comprise at least one covalent linkage between the peptides. The complex may be a covalently linked chimera between HIV1 Tat, fragments or derivatives thereof, and HIV Env, fragments or derivatives thereof, for example.

In one preferred complex, the binding region on the second peptide comprises amino acid residues 1-61 of Tat, or an immunological equivalent thereof. The Tat component may be a transactivation mutant.

It will be appreciated that preferred complexes are substantially free of cells and cellular detritus.

The invention further provides a method for the prevention or inhibition of HIV transmission from mother to child or between HIV-exposed individuals, comprising administering a passive vaccine as defined hereinto the mother or individual.

In general, the target virus for this treatment or prophylaxis will be a strain of HIV or HTLV, but also may be an animal strain, such as SHIV, for example.

Antibodies against complexes of the present invention may be raised by standard means, and suitable monoclonal or polyclonal antibodies, preferably monoclonal, generated. It is preferred that such antibodies are capable of binding none of CCR5, Tat, Env, or the V3 loop region of gp120, individually, but are capable of binding a complex of Tat and Env or co-receptor and Env. Thus, the resulting antibodies can bind and block complexes of Tat or co-receptor and Env in vivo, thereby preventing or inhibiting infection. It will be appreciated that such antibodies may not necessarily bind both, or all, of the components of the complex by interacting with new epitopes generated upon complex formation, and may simply bind cryptic epitopes exposed on binding of Tat with Env. Such epitopes may occur on Tat, Env or even CCR5, and this represents an advantage of the invention.

In the preparation of suitable antibodies against the complexes of the invention, antibodies that bind epitopes normally present on either Tat or Env can be removed by the simple expedient of eliminating antibodies or lines that bind Tat, Env, or the V3 loop of gp120, individually, from the polyclonal preparation or those monoclonal lines selected, thereby leaving only polyclonal preparations, or lines expressing antibodies, that bind epitopes present only in the complex.

It will be appreciated that monoclonal antibodies raised in this manner, if raised in animals, may be suitably humanised by methods well known in the art. The present invention extends to polyclonal, monoclonal and humanised antibodies specific for the complexes described herein.

Active vaccines comprising complexes of the invention are provided, as are antibody preparations for passive immunisation comprising antibodies of the invention, and vehicles suitable for such vaccines are well known in the art, and may comprise suitable substances, such as stabilisers, isotonic agents, and antibacterial agents.

The vehicle carrying the complex or antibody may be stored in a concentrated or inactive form, for dilution and/or activation as desired. Suitable vehicles may be saline or saline derivatives, or others readily apparent to those skilled in the art, and are preferably in injectable form, or may be made up into injectable form.

The amount of complex or antibody will be sufficient to serve as an immunogen or stimulant, or to have or boost biological effect, as appropriate.

The present invention also extends to the complexes themselves. One use of such complexes is in chromatographic techniques to establish whether a sample from a patient contains antibodies against the complex. The complex may be used in any conventional manner in such a technique, such as being fixed on a carrier for use in a column, a suitable detecting agent being a marked antiantibody, for example.

The complexes of the invention may further be used to target cells and to identify drugs interfering with HIV cellular entry, for example. A culture comprising the cells and the complex and subjected to an infective dose of virus can be assayed to establish whether, or how much, infection occurred, for example.

Thus, the Tat-V3 loop complex provides a novel antigen that can be used for preventive or therapeutic vaccination by inducing protective antibodies capable of blocking or binding the in vivo Tat-V3 loop interaction, thereby to disrupt subsequent infection. Antibodies may also block the CCR5-V3 loop interaction, and the complex may be used to generate protective antibodies for passive immunisation to block mother-to-child transmission or horizontal HIV transmission in exposed individuals, for example.

In a preferred embodiment, the present invention provides a molecular complex formed between the HIV Tat protein and the HIV envelope protein Env, which is generated upon the interaction of the cysteine rich and basic regions of Tat and the gp120 V3 loop. Molecular complexes obtained using the whole Tat protein, its mutants, fragments or derivatives thereof, and the HIV envelope protein gp160, fragments or derivatives thereof, are preferred, as are their use as antigens for preventive or therapeutic vaccination against HIV/AIDS.

A preferred complex comprises HIV Tat cysteine and basic region and the V3 loop of HIV Env. Since proteins are differentially processed by the proteasomes of cells exposed to Tat (Ensoli et al., PCT/EP2004/11950), another preferred complex comprises Tat fragments generated by the proteasomes of cells exposed to Tat, including fragments containing the cystein, basic and RGD regions of Tat, the cystein and basic regions of Tat, the basic and RGD region of Tat, or the basic region alone. Another comprises HIV Tat fragments or derivatives thereof and HIV Env fragments or derivatives thereof, while another comprises HIV Tat peptides or epitopes and HIV Env peptides or epitopes.

Also preferred is a: covalently linked chimera between HIV1 Tat, fragments or derivatives thereof, and HIV Env, fragments or derivatives thereof.

The Tat component, in one embodiment, may be a transactivation silent mutant, for example the Tat-cys$_{22}$ mutant.

The HIV of these embodiments is preferably HIV-1. Preferred clades are HIV-1 clades A, B, C, D, E, F, G, and O. It will be appreciated that the invention extends to CCR5-tropic, CXCR4 tropic and dual-tropic strains, and that reference to any specific virus, or type or class thereof, is equally applicable to all viruses subject of the invention.

The vaccines of the invention are of particular use in the prevention or inhibition of HIV transmission from mother to child or between HIV-exposed individuals.

The present invention is further illustrated by the following, non-limiting Examples.

EXAMPLE 1

Molecular Interaction of HIV-1 Tat with the Gp120 V3 Loop

The binding of HIV-1 Tat to the HIV-1 gp120 V3 loop was investigated using a molecular docking model, in which Tat (BH10 HIV strain) was allowed to interact with the V3 loop of the Env protein (Ba-L HIV strain). All structural models were calculated using, as template, all of the available structures of the Tat protein and of the Env protein deposited in the Protein Data Bank (Berman, H. M et al., *Nucl. Acids Res.* 28, 235-242, 2000) as of July 2003. The sequences of the various proteins were aligned using ClustalW (Thompson, J. D et al., *NucL Acids Res.* 22, 4673-4680, 1994) and the structural models were generated with Modeller6v2 (Sali, A. and Blundell, T. L. *J. Mol. Biol.* 234, 779-815, 1993). All of the calculated structural models were optimised through energy minimisation with AMBER-5 (Pearlman, D. A. et al., in *AMBER* 5.0, University of California, San Francisco, 1997). These structural models were then used to calculate the protein-protein adducts with the program BIGGER (Palma, P. N. et al., *Proteins Struct. Funct. Genet.* 39, 372-384, 2000). The latter program generates protein-protein complexes and ranks them on the basis of shape complementary and non-bonded (electrostatic and Van der Waals) interactions.

Initial molecular docking calculations were made with the isolated V3 loop (a.a. 297-336) and gave rise to three types of low energy adducts, characterised by three unique interaction regions. These adducts are characterised by different Tat residues interacting with the V3 loop although, by contrast, the V3 loop showed only a single interaction region involving residues Thr300, Arg301, Ala331, His332, Asn334, and several amino acids of the 306-328 segment of the V3 loop.

The interaction between Tat and a relatively large domain (291 a.a.) of HIV-1 Bal gp120 exposing the V3 loop was next calculated. As no structural information on the conformation of the V3 loop and its relative orientation with respect to the rest of the gp120 domain was available, the range of accessible conformations and the flexibility for V3 loop was sampled. The variability of the loop conformation can, in fact, have a sizable effect on the complex geometry. The conformation sampling was done through a long molecular dynamics simulation in explicit solvent. Docking calculations were performed, allowing Tat to interact with five different conformations of the gp120 of the Env protein including the two most different V3 loop conformations plus three intermediate conformations.

These calculations identified an adduct interacting with Tat in a region involving the V3 loop, which was essentially the same as that found in one of the adducts found with calculations performed with the V3 loop alone. This adduct was, therefore, predicted to be the most stable and was subjected to molecular dynamics (MD) calculations to optimise its conformation and to estimate its stability when a complete force field (produced by the atoms of the two molecules) is effective. The calculations were performed on both the oxidised (i.e. with disulphide bridge on V3 loop) and the reduced states of the Env protein, and showed that the adduct is similarly stable in both oxidation states. In order to validate the interaction model found with the described procedure, and to analyse the protein-protein interface, docking calculations with the program Haddock were also performed. The five lowest energy adducts were found to have the same geometry as the model found with the BIGGER calculations.

All these calculations, therefore, pointed at a unique mode of interaction. The final structural model of the adduct was found to be quite stable, with an average interaction surface of 2260±112 Å$^2$ and an average protein-protein intermolecular energy of −412±14 kcal mol$^{-1}$. The largest contribution to the interaction energy was due to the electrostatic contribution, with an average energy of −325±12 kcal mol$^{-1}$: the interaction surface involves residues 1, 2, 4, 16, 19-22, 25, 26, 29, 34, 35, 45-47, 51, 55, 57, 59, 61 on Tat and residues 301, 316, 317, 318, 321, 322, 324, 325, 327, 328, 329, 331, 332, 405, 407, 412, 416-419 on the Env.

Three intermolecular salt bridges between Tat and gp120 residues, respectively (Asp5-Arg316, Lys50-Glu407 and Lys19-Asp327) were found to be completely conserved in all of the various models and during the molecular dynamics simulations. The adduct was found to be further stabilised by additional intermolecular hydrogen bonds, which varied in number during the simulation from six to eleven, but always involving at least one residue of the common interaction region. A sizable contribution to the stabilisation of the adduct was also determined to be brought by 30 to 40 hydrophobic interactions. Twenty to thirty of these interactions were contributed by residues belonging to the V3 loop whereas about 20 of them by residues belonging to the 20-59 segment of Tat.

EXAMPLE 2

Tat Binds the Gp120 V3 Loop in an ELISA Assay.

Enzyme-linked immunosorbent assay (ELISA) tests were performed to determine whether Tat actually binds the gp120 V3 loop in vitro. To this purpose, ELISA plates were coated with a peptide encompassing the entire V3 loop, followed by extensive blocking with carrier bovine serum albumin (BSA), multiple washing steps, and additional incubation with biologically active Tat protein or, as a control, its buffer (PBS-BSA 0.1%) (Cafaro et al., Nat Med 1999; Fanales-Belasio et al., Immunology 2001). Monoclonal anti-V3 and polyclonal anti-Tat antibodies were used as primary antibodies for the detection of the bound protein.

When uncoated (i.e. BSA-blocked) wells were used in the ELISA assay with anti-Tat or anti-V3 antibodies, a slight background signal was detected, ranging from about 0.1 to 0.4 OD. The results are shown in Table 1, below. However, when wells coated with the V3 peptide were incubated with Tat, the signal was increased to about 1 optical density (OD). In contrast, wells incubated with buffer alone yielded signals comparable to background levels (uncoated wells). As expected, V3 coated wells yielded high ELISA signals with anti-V3 antibodies. These experiments show that biologically active Tat binds to the gp120 V3 loop in vitro, confirming the data obtained with molecular docking calculations. Similar results were obtained by coating wells with Tat and by incubating coated wells with increasing amounts of the V3 loop peptide, which, as expected, showed a dose-dependent binding of V3 loop peptide to immobilised Tat (Table 1bis).

TABLE 1

| Coating | Incubation | Antibodies | |
|---|---|---|---|
| | | anti-Tat | anti-V3 |
| none | buffer | 0.132 OD | 0.15 OD |
| none | Tat | 0.431 OD | 0.122 OD |
| V3 (500 ng) | buffer | 0.277 OD | 3 OD |
| V3 (500 ng) | Tat | 1 OD | 3 OD |

TABLE 1 bis

| V3 loop peptide amounts (ng) | 0 | 50 | 100 | 200 | 500 |
|---|---|---|---|---|---|
| Wells coated with Tat (100 ng) and blocked with bovine serum albumins (BSA) (100 μg) | | | | | |
| anti V3 antibody | 0.119 OD | 0.181 OD | 0.285 OD | 0.435 OD | 0.787 OD |
| anti TAT antibody | 1.438 OD | 1.545 OD | 1.51 OD | 1.515 OD | 1.567 OD |
| Wells coated with BSA (BSA) (100 μg) | | | | | |
| anti V3 antibody | 0.103 OD | 0.124 OD | 0.148 OD | 0.142 OD | 0.179 OD |

EXAMPLE 3

Tat is Recognised by Antibodies Directed Against the CCR5 HIV Co-Receptor

Since the gp120 V3 loop appears to be the major determinant for co-receptor choice and utilisation by HIV strains, experiments were performed to determine whether the capability of Tat to bind the V3 peptide was due to mimicry by Tat of co-receptor molecules. To this purpose, monoclonal antibodies directed against the major HIV-1 co-receptors (CCR5 and CXCR4) (Pharmingen) were used in an ELISA assay to determine whether they could recognise Tat, or Tat peptides consisting of specific Tat sequences and/or structural and functional domains. These monoclonal antibodies are known to recognise conformational epitopes present on HIV-1 co-receptors (Lee B et al., J Biol. Chem., 1999; Baribaud F et al., J Virol. 2001). Accordingly, any recognition of Tat by these antibodies would indicate that Tat shares structural similarity with the relevant co-receptor.

ELISA plates were coated either with native Tat or one of the following Tat peptides (the region or regions to which these peptides essentially correspond is given in parentheses):

Tat (1-20) (N-terminal domain);
Tat (21-40) (cysteine-rich region—transactivation domain);
Tat (36-50) (core region);
Tat (46-60) (basic region—nuclear localisation signal);
Tat (56-70) (glutamine-rich region);
Tat (65-80) (RGD sequence);
Tat (73-86) (ROD sequence);
Tat (83-102) (C-terminal domain); and
Tat (21-58) (cysteine, core, and basic regions).

Monoclonal anti-CCR5 or anti CXCR4 antibodies were used for the detection step. Anti-CCR5 specifically recognised the recombinant native Tat protein, the Tat (21-58) peptide and, although with a lower efficiency, the Tat (46-60) peptide. The results are shown in Table 2, below. In contrast, no recognition was observed with the antibodies directed against CXCR4.

TABLE 2

| | Antibodies | | | |
|---|---|---|---|---|
| Coating | anti-CCR5 | anti-CXCR4 | CTR isot. | anti-Tat |
| Tat | 1.452 | 0.085 | 0.081 | 3.000 |
| Tat 1-20 | 0.000 | 0.000 | 0.006 | 3.000 |
| Tat 21-40 | 0.000 | 0.133 | 0.082 | 0.1 |
| Tat 36-50 | 0.000 | 0.000 | 0.000 | 0.000 |
| Tat 46-60 | 0.466 | 0.000 | 0.063 | 0.000 |

TABLE 2-continued

| | Antibodies | | | |
|---|---|---|---|---|
| Coating | anti-CCR5 | anti-CXCR4 | CTR isot. | anti-Tat |
| Tat 56-70 | 0.147 | 0.000 | 0.000 | 0.75 |
| Tat 65-80 | 0.000 | 0.000 | 0.000 | 0.1 |
| Tat 73-86 | 0.000 | 0.077 | 0.019 | 0.087 |
| Tat 83-102 | 0.000 | 0.058 | 0.000 | 0.000 |
| Tat 21-58 | 3.000 | 0.072 | 0.108 | 0.551 |

The anti-CCR5 antibody used in these experiments is known to recognise a conformational epitope present in the CCR5 second extracellular loop (ECL2) and to be neutralising for HIV (Lee B et al., J Biol. Chem., 1999). In addition, RCL2 is known to be involved in the Env conformational changes leading to membrane fusion (Lee B et al., J Biol. Chem., 1999). Thus, these data indicated that Tat sequences encompassing both Tat transactivation domain and basic-rich region mimic at the structural level a region of the CCR5 involved in cell fusion upon recognition of CCR5 by gp120.

EXAMPLE 4

Native, Biologically Active Tat is Required for CCR5 Recognition by Anti-CCR5 Antibodies The data described in Example 3, above, indicate that Tat sequence present in peptide 21-58 is capable of folding to mimic a conformational epitope of the CCR5 co-receptor. To determine whether a specific conformation of Tat is required for recognition by the anti-CCR5 antibody, the capability of native, biologically active Tat to be recognised by the anti-CCR5 antibody was compared to an oxidised Tat preparation, obtained by exposing the protein to the air and direct light, according to a procedure known to abrogate most of its biological activity (Fanales-Belasio, Immunology, 2001). This procedure results in the oxidation of —SH groups and in the formation of intra- and intermolecular disulphide bounds, mediated by the cysteine residues present in the Tat transactivation domain. The transactivating properties of Tat, in turn, are known to activate the expression of host genes including HIV co-receptors (Huang 1998; Secchiero 1999). However, Tat transactivation properties are abolished in a transactivation mutant where cysteine 22 is substituted by a glycine (Tat-cys$_{22}$) (Caputo A et al., Gene Ther. 1996). This Tat mutant, nevertheless, maintains its immunogenic properties, intact (Caselli E et al., J Immunol. 1999). Thus, Tat-cys$_{22}$ was also included in this set of experiments.

ELISA wells were coated with native Tat, oxidised Tat (Tat OX) or Tat-cys$_{22}$ and the anti-CCR5, anti-CXCR4 antibody were used in the detection step. These experiments showed that the antibody specifically recognises the recombinant native Tat protein and the Tat-cys$_{22}$ mutant, but not the oxidised Tat protein. The results are shown in Table 3, below. In contrast, and as a control, polyclonal (rabbit) anti-Tat antibodies recognised, as expected, all proteins with similar efficiency, demonstrating that all wells were equally coated.

TABLE 3

| Coating | Antibodies | | | |
|---|---|---|---|---|
| | anti-CCR5 | anti-CXCR4 | CTR isot. | anti-Tat |
| Tat | 1.24 | 0.042 | 0.051 | 3 |
| Tat OX | 0.128 | 0.071 | 0.016 | 3 |
| Tat-cys22 | 0.75 | 0 | 0.026 | 3 |

These experiments showed, therefore, that Tat sequences encompassing the Tat transactivation domain, the core region and the basic region, fold to mimic a major epitope present on CCR5, and that a point mutation which abrogates the transactivating properties of Tat does not interfere with epitope formation.

EXAMPLE 5

Extracellular Tat Enhances Infection of CD4+ Susceptible Cells by HIV-1 and Expands HIV-1 Tropism in CCR5 Low Expression Cell Lines.

To determine whether Tat can mediate HIV-1 entry by mimicking CCR5, it was necessary to determine the effects of Tat on HIV entry in a CCR5-independent system. To this purpose, infection experiments were performed with a single cycle assay using a replication-defective recombinant HIV-1 encoding a cloramphenicol acetyltransferase (CAT) reporter gene and which was pseudotyped with the envelope glycoprotein of the CXCR4-tropic HXBc2 HIV isolate, or the CCR5-tropic ADA or YU2 HIV isolates. These replication-defective viruses (herein referred to as the R4-tropic HXBc2/HIV-CAT or the R5-tropic ADA/or YU2/HIV-CAT viruses) enter susceptible cells through CD4/CXCR4 or CD4/CCR5, integrate their cDNA's in the cell genome, and express the reporter gene CAT, but they can not produce progeny, i.e. they cannot support further infection of cells through subsequent cycles of virus production (Helseth E. J Virol 1990)). Thus, HIV-CAT viruses produce a single-round infection cycle of target cells, quantification of CAT acetylation levels allowing quantitative evaluation of the efficiency of HIV infection.

Based on the data obtained in Examples 1 to 4, above, experiments were performed to determine whether Tat could assist infection by HIV, expand HIV tropism, and render TCLs susceptible to infection by R5-tropic (i.e. monocyte/macrophage-tropic) HIV strains, owing to molecular mimicry of CCR5 co-receptor by Tat. To this purpose, CEMss and Jurkat cells, two TCLs expressing both CD4 and CXCR4, but lacking CCR5 expression at the protein level in amounts detectable by standard flow cytometry or Western blot, or the CD4-negative 293 cell line, were plated on Tat-coated wells that had previously been incubated with HIV-CAT viruses pseudotyped with the envelope from the X4-tropic HXBc2 strain, or the CCR5-tropic ADA or YU2 strains. As expected, both CEMss and Jurkat cell lines were efficiently infected with the HXBc2/HIV-CAT, whereas no infection was detected with the CD4-negative 293 cells, due to the lack of the primary HIV-1 receptor. Strikingly, furthermore, both CEMss and Jurkat cells were also infected at high efficiency by the ADA or YU2 pseudotyped HIV-CAT, despite being known to be resistant to infection by R5-tropic HIV-1 strains. These data, therefore, confirmed the unexpected prediction that immobilised. Tat is capable of increasing HIV-1 cell tropism through molecular mimicry of specific CCR5 extracellular structural domains, i.e., of rendering CCR5-tropic strains capable of infecting TCLs expressing such low amounts of CCR5 to be not consistently infected in. the absence of Tat.

Further experiments showed that Tat$_{21-58}$, but not Tat$_{21-40}$, was sufficient to assist infection of CEMss cells by the R5 tropic ADA Cat virus, showing that the region of Tat mediating binding to the gp120 V3 loop is the same as is required for HIV expanded tropism.

EXAMPLE 6

Anti-CCR5 Antibodies, but not Anti-CXCR4 Antibodies, Block Tat-Assisted Infection of Low CCR5 Expression Cell Lines To further demonstrate that immobilised Tat expands the cell tropism of R5-tropic HIV-1 strains by mimicking CCR5, experiments were performed to determine whether active molecules capable of blocking CCR5 were also capable of blocking Tat-assisted infection of CCR5-negative cells. To this purpose, the CD4+/CCR5− (CCR5 RT-PCR-positive) CEMss cells were plated in the presence of antibodies directed against CCR5, CXCR4 or CCR3 on Tat-coated wells which were previously incubated with cell supernatants containing the R5-tropic ADA/HIV-CAT single infection round recombinant virus. Tat assisted infection was almost completely abolished by anti-CCR5 antibody, whereas no reduction in infectivity was observed with anti-CXCR4 or CCR3 antibody as compared to control. Since CEMss cells are CCR5-negative at the protein level, these data indicate that the blocking activity of the antibodies is due to their capability of recognising Tat structural motifs mimicking CCR5 conformational epitopes, as detailed in Examples 3 and 4. Further, these data confirmed that molecular mimicry of CCR5 by Tat is required for entry of CCR5-tropic HIV-1 strains in CCR5-negative cells.

EXAMPLE 7

The Complexes Between Tat and Env are Novel Immunogens.

To determine whether Tat/Env complexes represent novel immunogens, i.e. that cryptic epitopes were being exposed, mice were immunised with mixtures of: Tat and Env proteins known to expose the V3 loop; Tat and the V3 loop peptide; or with the single antigens, as controls. The rationale of these experiments is based on the prediction that the B cell epitope determinant repertoire of the two antigens, combined, will be different, as compared to that for the single antigens, since new epitopes are generated, cryptic epitopes are exposed, and/or pre-existing epitopes are hidden upon complex formation. Accordingly, some complexes are predicted to broaden and/or to increase the intensity of the humoral responses against Tat and/or Env, and others to narrow/decrease at least part of them, depending on the nature of the complex and the B cell epitopes generated, exposed or hidden.

Three Env molecules were selected: wild type monomeric gp120 (wild type Env), which has been shown to generate more intense antibody responses against the V3 loop, owing to a better V3 loop exposure, as compared to the trimeric form present in the virus envelope (Fouts T R et al., J Virol 1997; Earl P L et al., J Virol 1994) a trimeric gp140 form of the Env molecule, which retains part of gp41 and is lacking the V2 loop (ΔV2Env) and is known to expose the V3 loop (Srivastava I K et al., J. Virol. 2003, Vol 77:11244-11259); and, a cyclic peptide corresponding to the V3 loop. To confirm the exposure of the V3 loop by the selected Env molecules, both monomeric wild type Env and trimeric ΔV2Env were tested by ELISA for reactivity against polyclonal anti-V3 loop sera, with positive results.

In a first 2-arm experiment, mice were immunised with Tat, wild-type Env, ΔV2Env, or the combination of Tat and wild-type Env, or Tat and ΔV2Env (in the presence of Alum as adjuvant) at days 0, 14 and 28. Humoral responses (IgG titres) were tested by ELISA on mouse sera obtained at day 38. Anti-Env IgG titres were strongly increased in mice vaccinated with Tat and ΔV2Env combined as compared to mice immunised with ΔV2Env alone. In contrast, they were comparable in mice immunised with wild type Env and Tat combined or with wild type Env alone. In addition, antibody titres against Tat were decreased upon combination with wild-type Env, but not upon combination with ΔV2Env. These data confirm that the combination of Tat ΔV2Env results in the formation of new molecular species (complexes) characterised by a new B cell epitope determinant repertoire. In addition, they show that the Tat/~V2Env complex has the capability to greatly increase anti-Env humoral responses, while protecting the elicitation of high anti-Tat antibody titres that, in contrast, are suppressed by wild type Env upon vaccination. Since monomeric wild type Env is shed in large amounts by HIV and infected cells, this is in agreement with the low frequency of anti-Tat antibodies in natural infection (Butta et al., J Infect Dis, 2002; Rezza et al., J Infect Dis, in press).

Mice were also immunised with Tat, V3 loop peptide, or the combination of Tat and V3 loop peptide in Alum. Of note, the V3 loop peptide alone was not immunogenic, eliciting no or borderline antibody titres, whereas the combination of Tat and V3 loop peptide highly increased antibody titres against the V3 loop with no effects on antibody titres against Tat.

Thus, these data demonstrate that Tat/Env or Tat/V3 loop complexes are novel immunogens, capable of eliciting higher and newer immune responses. In particular, the complex of Tat, together with ΔV2Env or V3 loop peptide, induces better humoral responses against HIV Env, and that these are different as compared to those elicited by the corresponding single antigens or by the complex between Tat and wild type Env.

EXAMPLE 8

Complexation of Tat and Env Changes Antibody Recognition of Individual Epitopes Present on Env To determine whether Tat/Env complexes induce humoral responses directed against Env epitopes different from those recognised upon immunisation with Env molecules alone, the sera from the same mice from the first immunisation protocol described in Example 7 were used to analyse reactivity to specific linear Env B cell epitopes. For this, 15-mer peptides spanning wild type Env or ΔV2 Env (SHIV-1 SF162.P3) were mixed together to form pools of peptides composed of three contiguous 15-mers (i.e., covering 45 aminoacids of Env or ΔV2 Env), and three 15-mers each overlapping the junction between two contiguous peptides.

Sera from mice immunised with wild type Env, or ΔV2 Env, combined with Tat, recognised linear epitopes present in between residues 77 to 132, i.e., spanning the first 14 amino acids of the HIV-1 V1 loop. In contrast, these epitopes were not recognised by sera from mice immunised with Env or ΔV2 Env used as single antigens. Consistent with deletion of the V2 loop in ΔV2 Env, only wild type Env elicited antibodies directed against the V2 loop, and reactivity was greatly increased upon combination with Tat. By contrast, immunisation with wild type Env alone elicited a strong reactivity against a region spanning residues 28 to 83 in HIV SF162 Env, that was completely lost upon co-immunisation with Tat. These data indicated, therefore, that the interaction between Tat and Env or DV2 Env exposes/hides linear Env/ΔV2 Env epitopes, consistent with complex formation.

Significantly, sera from mice immunised with Tat combined to ΔV2 Env, but not with ΔV2 Env alone, showed a strong reactivity against a region spanning the N and C helix of gp41, indicating conformational modifications of gp41 which are known to occur upon binding of Env to CD4 and, in turn, of V3 loop to CCR5 or other co-receptors, and which are known to be required and to precede the fusion of the virus envelope and the cell membrane. Therefore, these data are consistent with binding of Tat to the V3 loop, and with mimicry of CCR5 binding to Env, which is required for virus entry. Most importantly, these data indicate that the complex between Tat and ΔV2 Env can induce antibodies against HIV gp41, thereby being able to neutralise virus infectivity.

These linear gp41 epitopes are not recognised by sera from mice immunised with ΔV2 Env alone, indicating that the complex between Tat and ΔV2 Env is a new immunogen.

A similar change in epitope recognition is likely for conformational epitopes.

EXAMPLE 9

The Increase of Anti-Env Antibody Titres Upon Immunisation with Tat/ΔV2Env or V3 Loop Peptide Complexes is Due to Formation of New/Stronger B Cell Epitopes Present in the Complex, and not to the Increase of Th2 Responses Against Env.

It is well known in the art that T helper type 2 (Th2) responses, such as production of interleukin 4 (IL-4) by T cells, are key for generating humoral responses against antigens. Thus, at least part of the increase in anti-Env antibody titres elicited by immunisation with Tat combined with ΔV2Env or the V3 loop peptide might be explained, in addition to the generation of new epitopes on the complex, by increased and/or broadened Th2 responses against Env. Therefore, we investigated the effects of immunisation with Tat/ΔV2Env complexes on Th2 responses.

For this, mice immunised with a combination of Tat and ΔV2Env, or with ΔV2Env alone (see Example 7 for the protocol) were assessed for antigen-specific cellular responses against Env by IL-4 ELISPOT assay. This assay measures the production of IL-4, and is used in the art to evaluate Th2 responses against antigens or T cell-epitope peptides. Anti-Env cellular responses were assessed using matrices of pools of peptides containing Env 15-mers (overlapping by 11 amino acids) spanning the entire ΔV2Env molecule. These experiments showed that immunisation with ΔV2Env combined with Tat did not increase or broaden Th2 responses against Env, as compared to ΔV2Env alone, but elicited Th2 responses directed against the same Env epitopes. Therefore, these data indicate that the increase of antibody titres against Env upon immunisation with Tat combined with ΔV2Env or the V3 loop peptide is due to the generation/exposure of novel/stronger B cell epitopes upon complex formation.

EXAMPLE 10

Tat Broadens Cellular Responses to Env in Mice Co-Immunised with Both Antigens.

It is known that Tat can function as an adjuvant, increasing cell-mediated immune responses against antigens, and polarises the immune response toward a Th1 phenotype (Fanales Belasio et al., J Immunol 2002; Ensoli B., WO03/009867). In addition, Tat broadens Th1 responses against antigens by altering their processing by the proteasome (Ensoli et al., PCT/EP2004/11950). This results in the induction of responses against antigenic cytotoxic T cell (CTL) epitopes that are normally sub-dominant (Ensoli et al., PCT/EP2004/11950).

To investigate the effects of immunisation with Tat and Env combined in a complex on Th1 responses and polarisation by Tat, production of γIFN (a typical Th1 cytokine) by spleen cells from mice immunised with the combination of Tat and ΔV2Env, or with ΔV2Env alone, were analysed using matrices of pools of peptides containing Env 15-mers (overlapping by 11 amino acids) (see example 7 for the protocol). Anti-Env g-ELISPOTS displayed Env-specific T cell responses against a larger number of peptide pools and epitopes (not shown) in mice immunised with Tat+ΔV2Env, as compared to mice immunised with ΔV2Env alone. These data indicate that Tat combined with ΔV2Env maintains the capacity to broaden Th1 responses against Env in immunised mice, as already shown for Tat combined with wild-type Env (Ensoli et al., PCT/EP2004/11950). Therefore, Env complexes can be used as immunogens to induce effective/neutralising humoral responses and, at the same time, to broaden CTL responses against Env.

The invention claimed is:

1. A complex comprising a first peptide and a second peptide bound thereto, the first peptide comprising the V3 loop of gp120, wherein the V3 loop is exposed and thereby bound to a binding region on the second peptide to form the complex, the second peptide comprising said binding region which region comprises at least residues 21-40 and 46-58 of Tat (SEQ ID NO 1), or at least said residues with a further point mutation whereby Cys 22 of Tat is replaced by Glycine to produce a Tat Cys22 mutant,
   wherein the first peptide comprising the V3 loop is selected from the group consisting of:
   an isolated V3 loop peptide of gp120;
   a peptide consisting of residues 299-333 of SEQ ID NO. 2; and
   the trimeric gp140 form of Env, retaining part of gp41 and lacking the V2 loop of Env,
   and optionally wherein the complex further comprises a molecule or substance capable of interacting with Env to expose a functional V3 loop or the peptides are cross-linked.

2. The complex of claim 1, the binding region on the second peptide being derived from Tat and being recognisable by a monoclonal antibody directed against the CCR5 second extracellular loop.

3. The complex of claim 1, wherein the binding region comprises at least residues 21-58 of Tat as set forth in SEQ ID NO 1, or a TatCys22 mutant thereof.

4. The complex of claim 1, prepared with native Tat.

5. The complex of claim 1, wherein the peptide comprising the V3 loop comprises some of gp120 in addition to the V3 loop.

6. The complex of claim 1, wherein the first peptide consists of the V3 loop region of gp120.

7. The complex of claim 1, wherein the first peptide is the trimeric gp140 form of Env, retaining part of gp41 and lacking the V2 loop of Env.

8. The complex of claim 1, further comprising a molecule or substance capable of interacting with Env to expose a functional V3 loop, wherein said molecule or substance is CD4 and interacts with Env to expose a functional V3 loop.

9. The complex of claim 1, further comprising a heparin sulphate.

10. The complex of claim 1, further comprising a substance selected from the group consisting of integrins, basic fibroblast growth factor, CD26, VEGF receptors, and chemokine receptors.

11. The complex of claim 1, wherein the binding region is contained within a fragment of Tat generatable by proteasomes of human cells on exposure to Tat, wherein the Tat fragment is selected from the group consisting of fragments containing the cysteine, basic and RGD regions of Tat; fragments containing the cysteine and basic regions of Tat; fragments containing the basic and RGD region of Tat; and, fragments containing the basic region of Tat, alone.

12. The complex of claim 1, wherein said peptides are cross-linked.

13. A vehicle suitable for injection comprising the complex of claim 1.

14. A kit comprising at least two separate preparations of the components of the complex of claim 1.

15. A method for inducing antibodies to HIV which comprises administering the complex of claim 1 to a patient in need thereof.

16. A method for inducing antibodies to HIV in a patient in need, whereby the HIV expresses a molecule capable of forming a ternary complex between said molecule, CD4 and CCR5, comprising administering the complex of claim 1 to the patient.

17. A method to establish whether a sample from a patient contains antibodies against the complex of claim 1 which comprises contacting said complex with said sample and detecting the presence of antibodies bound to said complex.

18. A complex according to claim 1, wherein the second peptide comprises at least residues 21-60 of Tat (SEQ ID NO: 1) with a further point mutation whereby a residue corresponding to Cys 22 of Tat in SEQ ID NO: 1 is replaced by Glycine.

19. An immunogenic complex comprising a first peptide and a second peptide bound thereto,
   the first peptide comprising, at least the V3 loop of gp120 and lacks at least the majority of the V2 loop of gp120, wherein the first peptide forms a trimer, and wherein the V3 loop is exposed and thereby bound to a binding region on the second peptide to form the complex, MD
   the second peptide comprising said binding region which region comprises at least residues 21-40 and 46-58 of Tat (SEQ ID NO 1), or at least said residues with a further point mutation whereby Cys 22 of Tat is replaced by Glycine to produce a TatCys22 mutant;
   wherein the complex further comprises a molecule or substance capable of interacting with Env to expose a functional V3 loop or the peptides are cross-linked.

20. A complex according to claim 19, wherein said molecule or substance is CD4 capable of interacting with Env to expose a functional V3 loop.

21. A complex according to claim 19, wherein the molecule or substance is a heparin sulphate.

22. The complex of claim 1, wherein said molecule or substance is CD4 capable of interacting with Env to expose a functional V3 loop.

23. An immunogenic complex comprising a first peptide and a second peptide bound thereto, wherein the first peptide is a gp160 molecule comprising at least the V3 loop of gp120 and lacking at least the majority of the V2 loop of gp120, wherein the first peptide forms a trimer, and wherein the V3 loop is exposed and thereby bound to a binding region on the second peptide to form the complex,
   the second peptide comprising said binding region which region comprises at least residues 21-40 and 46-58 of Tat (SEQ ID NO 1), or at least said residues with a further point mutation whereby Cys 22 of Tat is replaced by Glycine to produce a Tat Cys22 mutant.

* * * * *

UNITED STATES PATENT AND TRADEMARK OFFICE
CERTIFICATE OF CORRECTION

PATENT NO. : 9,969,780 B1
APPLICATION NO. : 10/597926
DATED : May 15, 2018
INVENTOR(S) : Barbara Ensoli It is certified that error appears in the above-identified patent and that said Letters Patent is hereby corrected as shown below:

In the Claims

In Claim 19, Column 26, Line 38, delete "MD".

Signed and Sealed this
Seventh Day of August, 2018

Andrei Iancu
*Director of the United States Patent and Trademark Office*

```
SEQUENCE LISTING

<160> NUMBER OF SEQ ID NOS: 2

<210> SEQ ID NO 1
<211> LENGTH: 102
<212> TYPE: PRT
<213> ORGANISM: Human immunodeficiency virus type 1

<400> SEQUENCE: 1

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Arg Pro Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu Gln Lys Lys Lys Val Glu Arg Glu Thr Glu
                85                  90                  95

Thr Asp Pro Val His Gln
            100

<210> SEQ ID NO 2
<211> LENGTH: 853
<212> TYPE: PRT
<213> ORGANISM: Human immunodeficiency virus type 1
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (84)..(86)
<223> OTHER INFORMATION: Xaa can be any naturally occurring amino acid
<220> FEATURE:
<221> NAME/KEY: misc_feature
```

```
<222> LOCATION: (138)..(139)
<223> OTHER INFORMATION: Xaa can be any naturally occurring amino acid
<220> FEATURE:
<221> NAME/KEY: misc_feature
<222> LOCATION: (141)..(141)
<223> OTHER INFORMATION: Xaa can be any naturally occurring amino acid
<220> FEATURE:
<221> NAME/KEY: misc_feature
<222> LOCATION: (143)..(143)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (167)..(167)
<223> OTHER INFORMATION: Xaa can be any naturally occurring amino acid
<220> FEATURE:
<221> NAME/KEY: misc_feature
<222> LOCATION: (190)..(190)
<223> OTHER INFORMATION: Xaa can be any naturally occurring amino acid
<220> FEATURE:
<221> NAME/KEY: misc_feature
<222> LOCATION: (243)..(243)
<223> OTHER INFORMATION: Xaa can be any naturally occurring amino acid
<220> FEATURE:
<221> NAME/KEY: misc_feature
<222> LOCATION: (278)..(278)
<223> OTHER INFORMATION: Xaa can be any naturally occurring amino acid
<220> FEATURE:
<221> NAME/KEY: misc_feature
<222> LOCATION: (281)..(281)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid
<220> FEATURE:
<221> NAME/KEY: misc_feature
<222> LOCATION: (349)..(349)
<223> OTHER INFORMATION: Xaa can be any naturally occurring amino acid
<220> FEATURE:
<221> NAME/KEY: misc_feature
<222> LOCATION: (426)..(426)
<223> OTHER INFORMATION: Xaa can be any naturally occurring amino acid
<220> FEATURE:
<221> NAME/KEY: misc_feature
<222> LOCATION: (674)..(674)
<223> OTHER INFORMATION: Xaa can be any naturally occurring amino acid
<220> FEATURE:
<221> NAME/KEY: misc_feature
<222> LOCATION: (751)..(751)
<223> OTHER INFORMATION: Xaa can be any naturally occurring amino acid
<220> FEATURE:
<221> NAME/KEY: misc_feature
<222> LOCATION: (761)..(761)
<223> OTHER INFORMATION: Xaa can be any naturally occurring amino acid
<220> FEATURE:
<221> NAME/KEY: misc_feature
<222> LOCATION: (795)..(795)
<223> OTHER INFORMATION: Xaa can be any naturally occurring amino acid
<220> FEATURE:
<221> NAME/KEY: misc_feature
<222> LOCATION: (814)..(815)
<223> OTHER INFORMATION: Xaa can be any naturally occurring amino acid
<220> FEATURE:
<221> NAME/KEY: misc_feature
<222> LOCATION: (817)..(817)
<223> OTHER INFORMATION: Xaa can be any naturally occurring amino acid
<220> FEATURE:
<221> NAME/KEY: misc_feature
<222> LOCATION: (830)..(830)
<223> OTHER INFORMATION: Xaa can be any naturally occurring amino acid

<400> SEQUENCE: 2

Met Arg Val Thr Glu Ile Arg Lys Ser Tyr Gln His Trp Trp Arg Trp
1               5                   10                  15
```

```
Gly Ile Met Leu Leu Gly Xaa Leu Met Ile Cys Asn Ala Glu Glu Lys
                20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
50                  55                  60

His Asn Val Trp Ala Thr His Ala Cys Val Pro Thr Asp Pro Asn Pro
65                  70                  75                  80

Gln Glu Val Xaa Xaa Xaa Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Leu Arg Asn Ala Thr Xaa Xaa Asn Xaa Thr Xaa Thr
    130                 135                 140

Thr Ser Ser Ser Arg Gly Met Val Gly Gly Gly Glu Xaa Lys Asn Cys
145                 150                 155                 160

Ser Phe Asn Ile Thr Thr Xaa Ile Arg Gly Lys Val Gln Lys Glu Tyr
                165                 170                 175

Ala Leu Phe Tyr Glu Leu Asp Ile Val Pro Ile Asp Asn Xaa Ile Asp
            180                 185                 190

Arg Tyr Arg Leu Ile Ser Cys Asn Thr Ser Val Ile Thr Gln Ala Cys
        195                 200                 205

Pro Lys Val Ser Phe Glu Pro Ile Pro Ile His Tyr Cys Ala Pro Ala
    210                 215                 220

Gly Phe Ala Ile Leu Lys Cys Lys Asp Lys Lys Phe Asn Gly Lys Gly
225                 230                 235                 240

Pro Cys Xaa Asn Val Ser Thr Val Gln Cys Thr His Gly Ile Arg Pro
                245                 250                 255

Val Val Ser Thr Gln Leu Leu Leu Asn Gly Ser Leu Ala Glu Glu Glu
            260                 265                 270

Val Val Ile Arg Ser Xaa Asn Phe Xaa Asx Asn Ala Lys Xaa Ile Ile
        275                 280                 285

Val Gln Leu Asn Glu Ser Val Glu Ile Asn Cys Thr Arg Pro Asn Asn
    290                 295                 300

Asn Thr Arg Lys Ser Ile His Ile Gly Pro Gly Arg Ala Phe Tyr Thr
305                 310                 315                 320

Thr Gly Glu Ile Ile Gly Asp Ile Arg Gln Ala His Cys Asn Leu Ser
                325                 330                 335

Arg Ala Lys Trp Asn Asp Thr Leu Asn Lys Ile Val Xaa Lys Leu Arg
            340                 345                 350

Glu Gln Phe Gly Asn Lys Thr Ile Val Phe Lys His Ser Ser Gly Gly
        355                 360                 365

Asp Pro Glu Ile Val Thr His Ser Phe Asn Cys Gly Gly Glu Phe Phe
    370                 375                 380

Tyr Cys Asn Ser Thr Gln Leu Phe Asn Ser Thr Trp Asn Val Thr Glu
385                 390                 395                 400

Glu Ser Asn Asn Thr Val Glu Asn Asn Thr Ile Thr Leu Pro Cys Arg
                405                 410                 415

Ile Lys Gln Ile Ile Asn Met Trp Gln Xaa Val Gly Arg Ala Met Tyr
            420                 425                 430
```

-continued

```
Ala Pro Pro Ile Arg Gly Gln Ile Arg Cys Ser Ser Asn Ile Thr Gly
            435                 440                 445

Leu Leu Leu Thr Arg Asp Gly Pro Glu Asp Asn Lys Thr Glu Val
        450                 455                 460

Phe Arg Pro Gly Gly Asp Met Arg Asp Asn Trp Arg Ser Glu Leu
465                 470                 475                 480

Tyr Lys Tyr Lys Val Val Lys Ile Glu Pro Leu Gly Val Ala Pro Thr
                485                 490                 495

Lys Ala Lys Arg Val Val Gln Arg Glu Lys Arg Ala Val Gly Ile
            500                 505                 510

Gly Ala Val Phe Leu Gly Phe Leu Gly Ala Ala Gly Ser Thr Met Gly
            515                 520                 525

Ala Ala Ser Met Thr Leu Thr Val Gln Ala Arg Leu Leu Leu Ser Gly
            530                 535                 540

Ile Val Gln Gln Gln Asn Asn Leu Leu Arg Ala Ile Glu Ala Gln Gln
545                 550                 555                 560

His Leu Leu Gln Leu Thr Val Trp Gly Ile Lys Gln Leu Gln Ala Arg
                565                 570                 575

Val Leu Ala Val Glu Arg Tyr Leu Arg Asp Gln Gln Leu Leu Gly Ile
            580                 585                 590

Trp Gly Cys Ser Gly Lys Leu Ile Cys Thr Thr Ala Val Pro Trp Asn
            595                 600                 605

Ala Ser Trp Ser Asn Lys Ser Leu Asn Lys Ile Trp Asp Asn Met Thr
            610                 615                 620

Trp Met Glu Trp Asp Arg Glu Ile Asn Asn Tyr Thr Ser Ile Ile Tyr
625                 630                 635                 640

Ser Leu Ile Glu Glu Ser Gln Asn Gln Gln Glu Lys Asn Glu Gln Glu
                645                 650                 655

Leu Leu Glu Leu Asp Lys Trp Ala Ser Leu Trp Asn Trp Phe Asp Ile
            660                 665                 670

Thr Xaa Trp Leu Trp Tyr Ile Lys Ile Phe Ile Met Ile Val Gly Gly
            675                 680                 685

Leu Ile Gly Leu Arg Ile Val Phe Ser Val Leu Ser Ile Val Asn Arg
            690                 695                 700

Val Arg Gln Gly Tyr Ser Pro Leu Ser Phe Gln Thr His Leu Pro Ala
705                 710                 715                 720

Ser Arg Gly Pro Asp Arg Pro Gly Gly Ile Glu Glu Glu Gly Gly Glu
                725                 730                 735

Arg Asp Arg Asp Arg Ser Gly Pro Leu Val Asn Gly Phe Leu Xaa Leu
            740                 745                 750

Ile Trp Val Asp Leu Arg Ser Leu Xaa Leu Phe Ser Tyr His Arg Leu
            755                 760                 765

Arg Asp Leu Leu Leu Ile Val Thr Arg Ile Val Glu Leu Leu Gly Arg
            770                 775                 780

Arg Gly Trp Glu Val Leu Lys Tyr Trp Trp Xaa Leu Leu Gln Tyr Trp
785                 790                 795                 800

Ser Gln Glu Leu Lys Asn Ser Ala Val Ser Leu Leu Asn Xaa Xaa Ala
                805                 810                 815
```

```
Xaa Ala Val Ala Glu Gly Thr Asp Arg Val Ile Glu Val Xaa Gln Arg
            820                 825                 830

Ala Val Arg Ala Ile Leu His Ile Pro Arg Arg Ile Arg Gln Gly Leu
            835                 840                 845

Glu Arg Ala Leu Leu
    850
```